(12) United States Patent
Huang et al.

(10) Patent No.: US 12,203,093 B2
(45) Date of Patent: Jan. 21, 2025

(54) DIGITAL-TO-ANALOG CONVERSION APPARATUS AND METHOD HAVING SIGNAL CALIBRATION MECHANISM

(71) Applicant: REALTEK SEMICONDUCTOR CORPORATION, Hsinchu (TW)

(72) Inventors: Liang-Wei Huang, Hsinchu (TW); Hsuan-Ting Ho, Hsinchu (TW); Shih-Hsiung Huang, Hsinchu (TW)

(73) Assignee: REALTEK SEMICONDUCTOR CORPORATION, Hsinchu (TW)

( * ) Notice: Subject to any disclaimer, the term of this patent is extended or adjusted under 35 U.S.C. 154(b) by 176 days.

(21) Appl. No.: 18/106,638

(22) Filed: Feb. 7, 2023

(65) Prior Publication Data
US 2023/0183744 A1   Jun. 15, 2023

(30) Foreign Application Priority Data
May 10, 2022   (TW) .................. 111117527

(51) Int. Cl.
*C12N 15/86* (2006.01)
*H03M 1/08* (2006.01)
*H03M 1/10* (2006.01)

(52) U.S. Cl.
CPC .............. *C12N 15/86* (2013.01); *H03M 1/08* (2013.01); *H03M 1/1014* (2013.01); *H03M 1/1042* (2013.01); *C12N 2740/10041* (2013.01); *C12N 2740/10052* (2013.01); *C12N 2740/13051* (2013.01); *C12N 2740/13052* (2013.01); *C12N 2740/15051* (2013.01);

(Continued)

(58) Field of Classification Search
CPC ...... C12N 15/86; H03M 1/08; H03M 1/1014; H03M 1/1042; H03M 1/1023
See application file for complete search history.

(56) References Cited

U.S. PATENT DOCUMENTS

2011/0150067 A1*  6/2011  Takada ................. H04R 3/02
                                                            375/350

OTHER PUBLICATIONS

U.S. Appl. No. 17/728,178 (USPTO receipt date: Apr. 25, 2022) 1-1) 17728178_spec 1-2) 17728178_drawing 1-3) 17728178_efilingAck45552080.

(Continued)

*Primary Examiner* — Joseph J Lauture
(74) *Attorney, Agent, or Firm* — WPAT, PC (57) ABSTRACT

The present invention discloses a digital-to-analog conversion apparatus having signal calibration mechanism. A DAC circuit includes conversion circuits to generate an output analog signal and an echo-canceling analog signal. An echo transmission circuit performs signal processing on an echo path to generate an echo signal. An echo calibration circuit includes odd and even calibration circuits to perform mapping according to offset tables and perform processing according to response coefficients on odd and even input parts of an input digital signal to generate odd and even calibration parts of an echo-canceling calibration signal. A calibration parameter calculation circuit generates offsets according to an error signal between the echo signal and the echo-canceling calibration signal and path information related to the echo calibration circuit. The echo calibration circuit makes the coefficients converge according to the error signal and pseudo noise transmission path information, and updates the offset tables according to the offset.

18 Claims, 5 Drawing Sheets

(52) U.S. Cl.
CPC .............. *C12N 2740/15052* (2013.01); *C12N 2740/16051* (2013.01); *C12N 2740/16052* (2013.01)

(56) References Cited

OTHER PUBLICATIONS

U.S. Appl. No. 18/105,675 (USPTO receipt date: Feb. 3, 2023) 2-1) 18105675_spec 2-2) 18105675_drawing 2-3) 18105675_efilingAck47479967.

\* cited by examiner

DIGITAL-TO-ANALOG CONVERSION APPARATUS AND METHOD HAVING SIGNAL CALIBRATION MECHANISM

BACKGROUND OF THE INVENTION

1. Field of the Invention

The present invention relates to a digital-to-analog conversion apparatus and a digital-to-analog conversion method having signal calibration mechanism.

2. Description of Related Art

A digital-to-analog conversion apparatus is an important circuit component to convert a signal from a digital form to an analog form. The digital-to-analog conversion apparatus multiply different digital codes by corresponding conversion gain values to generate analog signals having different intensities.

However, an error is generated in the digital-to-analog conversion apparatus due to offsets of current sources therein. Further, an echo is generated due to the mismatch of a transmission path that transmits the signal. Different calibration technologies are required for the digital-to-analog conversion apparatus to perform calibration on the input and output signals to accomplish a better conversion result.

SUMMARY OF THE INVENTION

In consideration of the problem of the prior art, an object of the present invention is to supply a digital-to-analog conversion apparatus and a digital-to-analog conversion method having signal calibration mechanism.

The present invention discloses a digital-to-analog conversion apparatus having signal calibration mechanism that includes a digital-to-analog conversion circuit, an echo transmission circuit, an echo calibration circuit and a calibration parameter calculation circuit. The digital-to-analog conversion circuit includes a plurality of conversion circuits operating at a first frequency to perform conversion according to a signal feeding related to an input digital signal having an input codeword to generate an output analog signal and an echo-canceling analog signal, wherein the echo-canceling analog signal at least performs output echo-canceling on the output analog signal at an echo path. The echo transmission circuit performs signal processing that includes down-sampling on the echo path to generate an echo signal having a second frequency, wherein the second frequency is a half of the first frequency. The echo calibration circuit includes an odd calibration circuit and an even calibration circuit operating at the second frequency and corresponding to the conversion circuits that generate the echo-canceling analog signal, wherein the odd calibration circuit and the even calibration circuit perform mapping according to a plurality of offset tables and perform processing according to a plurality groups of response coefficients on the signal feeding related to an odd input part and an even input part of the input digital signal respectively, to generate an odd calibration part and an even calibration part of an echo-canceling calibration signal. The calibration parameter calculation circuit operating at the second frequency generates a plurality offsets according to an error signal between the echo signal and the echo-canceling calibration signal and path information related to the echo calibration circuit, wherein the echo calibration circuit makes the groups of response coefficients converge according to the error signal and pseudo noise transmission path information from the digital-to-analog conversion circuit to the echo transmission circuit, and further updates the offset tables according to the offsets.

The present invention also discloses a digital-to-analog conversion method having signal calibration mechanism used in a digital-to-analog conversion apparatus that includes steps outlined below. Conversion is performed according to a signal feeding related to an input digital signal having an input codeword to generate an output analog signal and an echo-canceling analog signal by a digital-to-analog conversion circuit such that the echo-canceling analog signal at least performs output echo-canceling on the output analog signal at an echo path, wherein the digital-to-analog conversion circuit includes a plurality of conversion circuits operating at a first frequency. Signal processing that includes down-sampling is performed on the echo path to generate an echo signal having a second frequency by an echo transmission circuit, wherein the second frequency is a half of the first frequency. Mapping is performed according to a plurality of offset tables and processing is performed according to a plurality groups of response coefficients on the signal feeding related to an odd input part and an even input part of the input digital signal respectively by an echo calibration circuit, to generate an odd calibration part and an even calibration part of an echo-canceling calibration signal, wherein the echo calibration circuit comprises an odd calibration circuit and an even calibration circuit operating at the second frequency and corresponding to the conversion circuits that generate the echo-canceling analog signal. A plurality offsets are generated according to an error signal between the echo signal and the echo-canceling calibration signal and path information related to the echo calibration circuit by a calibration parameter calculation circuit operating at the second frequency. The groups of response coefficients are converged according to the error signal and pseudo noise transmission path information from the digital-to-analog conversion circuit to the echo transmission circuit and the offset tables are further updated according to the offsets by the echo calibration circuit.

These and other objectives of the present invention will no doubt become obvious to those of ordinary skill in the art behind reading the following detailed description of the preferred embodiments that are illustrated in the various figures and drawings.

DETAILED DESCRIPTION OF THE PREFERRED EMBODIMENTS

An aspect of the present invention is to provide a digital-to-analog conversion apparatus and a digital-to-analog conversion method having signal calibration mechanism to generate an output analog signal and an echo-canceling analog signal having a first frequency and perform calibration thereon by using internal circuits that operate in a second frequency, which is a half of the first frequency according to an echo signal through down-sampling.

Figure 1:
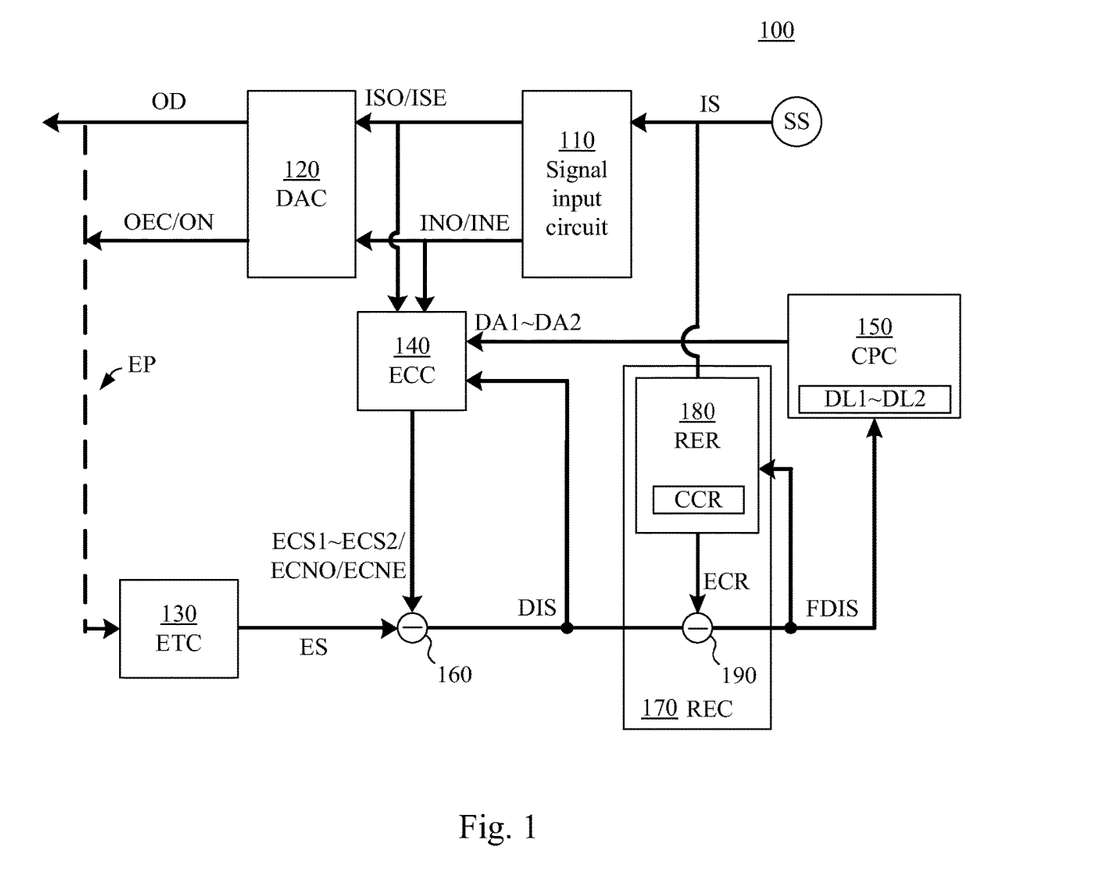
FIG. 1 illustrates a circuit diagram of a digital-to-analog conversion apparatus having signal calibration mechanism according to an embodiment of the present invention.

Reference is now made to FIG. 1. FIG. 1 illustrates a circuit diagram of a digital-to-analog conversion apparatus 100 having signal calibration mechanism according to an embodiment of the present invention. The digital-to-analog conversion apparatus 100 includes a signal input circuit 110, a digital-to-analog conversion circuit 120 (abbreviated as DAC in FIG. 1), an echo transmission circuit 130 (abbreviated as ETC in FIG. 1), an echo calibration circuit 140 (abbreviated as ECC in FIG. 1) and a calibration parameter calculation circuit 150 (abbreviated as CPC in FIG. 1).

The signal input circuit 110 performs signal feeding on the digital-to-analog conversion circuit 120. The digital-to-analog conversion circuit 120 includes a plurality of conversion circuits operating at a first frequency, wherein the first frequency is such as, but not limited to 800 MHz. The digital-to-analog conversion circuit 120 performs digital-to-analog conversion according to a signal feeding related to an input digital signal IS having an input codeword to generate an output analog signal OD and an echo-canceling analog signal. The echo-canceling analog signal at least performs output echo-canceling on the output analog signal OD at an echo path EP.

The operation of the signal input circuit 110 and the digital-to-analog conversion circuit 120 is described in the following paragraphs in accompany with FIG. 2 and FIG. 3.

Figure 2:
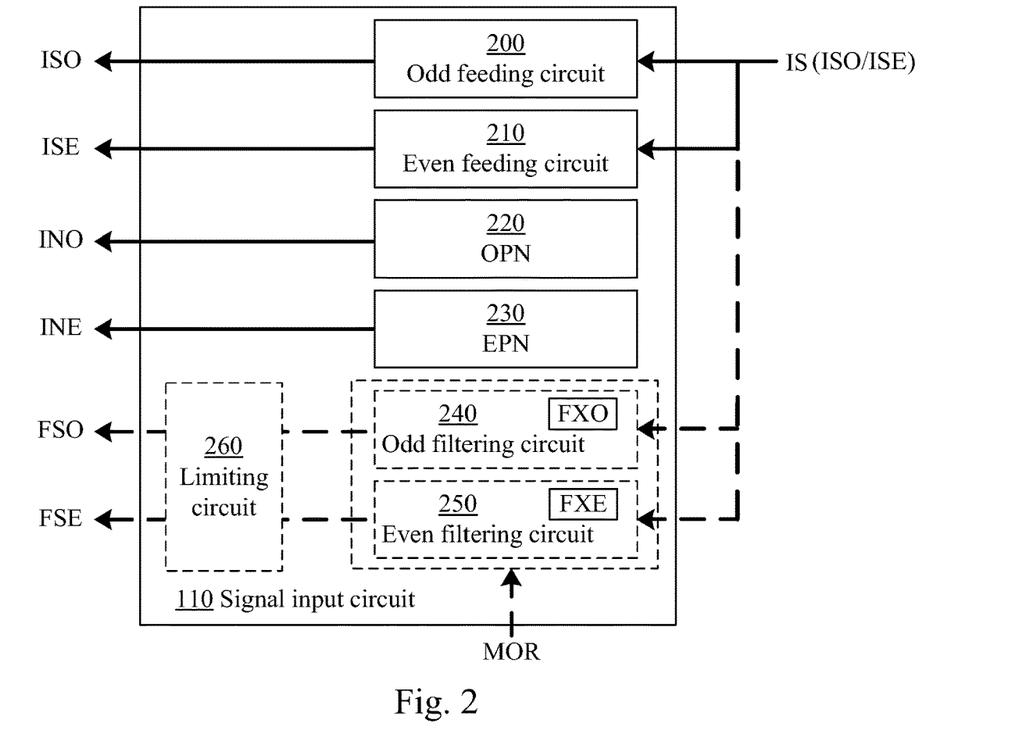
FIG. 2 illustrates a more detailed block diagram of the signal input circuit according to an embodiment of the present invention.

FIG. 2 illustrates a more detailed block diagram of the signal input circuit 110 according to an embodiment of the present invention. The signal input circuit 110 includes an odd feeding circuit 200, an even feeding circuit 210 an odd pseudo noise generation circuit 220 (abbreviated as OPN in FIG. 2) and an even pseudo noise generation circuit 230 (abbreviated as EPN in FIG. 2).

Figure 3:
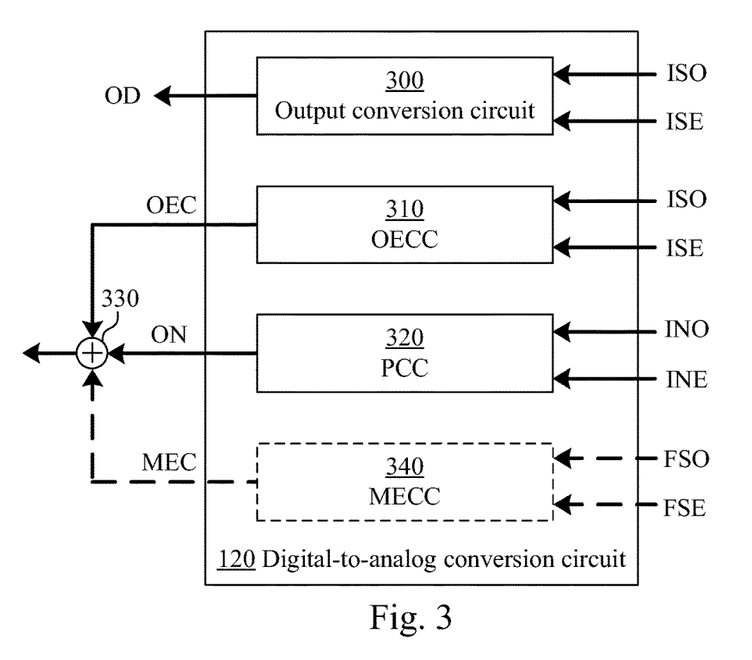
FIG. 3 illustrates a more detailed block diagram of the digital-to-analog conversion circuit according to an embodiment of the present invention.

FIG. 3 illustrates a more detailed block diagram of the digital-to-analog conversion circuit 120 according to an embodiment of the present invention. The conversion circuits of the digital-to-analog conversion circuit 120 include an output conversion circuit 300, an output echo-canceling conversion circuit 310 (abbreviated as OECC in FIG. 3) and a pseudo noise conversion circuit 320 (abbreviated as PCC n FIG. 3).

The odd feeding circuit 200 retrieves and outputs an odd input part ISO of the input digital signal IS. The even feeding circuit 210 retrieves and outputs an even input part ISE of the input digital signal IS. As a result, when the input digital signal IS has a first frequency, each of the odd input part ISO and the even input part ISE has a second frequency, in which the value of the second frequency is about the half of the value of the first frequency. Take the example of the value described above, the second frequency is 400 MHz under the condition that the first frequency is 800 MHz.

In an embodiment, the odd feeding circuit 200 and the even feeding circuit 210 receive the input digital signal IS from a signal source SS in FIG. 1, which is such as a transmitter (TX) in a communication system. Further, each of the odd feeding circuit 200 and the even feeding circuit 210 can be implemented by a filter circuit to perform filtering on and output the odd input part ISO and the even input part ISE.

The output conversion circuit 300 receives and performs conversion on the odd input part ISO and the even input part ISE to generate the output analog signal OD. The output echo-canceling conversion circuit 310 also receives and performs conversion on the odd input part ISO and the even input part ISE to generate an output echo-canceling analog signal OEC included in the echo-canceling analog signal. The output analog signal OD is the signal actually transmitted to an external terminal. However, the output analog signal OD may be leaked to a receiver (RX, not illustrated in the figure) through the echo path EP in FIG. 1. As a result, the output echo-canceling analog signal OEC performs echo-canceling on the output analog signal OD leaked to the echo path EP.

The odd pseudo noise generation circuit 220 generates and feeds an odd pseudo noise digital signal INO to the digital-to-analog conversion circuit 120. The even pseudo noise generation circuit 230 generates and feeds an even pseudo noise digital signal INE to the digital-to-analog conversion circuit 120. In an embodiment, each of the odd pseudo noise digital signal INO and the even pseudo noise digital signal INE is a random signal of 0 and 1 that simulates a noise.

The pseudo noise conversion circuit 320 receives and performs conversion on the odd pseudo noise digital signal INO and the even pseudo noise digital signal INE to generate a pseudo noise analog signal ON to the echo path EP. The generation of the odd pseudo noise digital signal INO and the even pseudo noise digital signal INE and the feedback of the pseudo noise analog signal ON are used to measure a response from the digital-to-analog conversion circuit 120 to the echo path EP.

In an embodiment, the digital-to-analog conversion circuit 120 further includes an adding circuit 330 that adds the analog signals described above and transmits the added result to the echo path EP in FIG. 1 to perform echo-canceling on the output analog signal OD leaked to the echo path EP.

The echo transmission circuit 130 in FIG. 1 performs signal processing that includes down-sampling on the echo path EP to generate an echo signal ES having a second frequency, wherein the second frequency is a half of the first frequency. The signal processing includes such as but not limited to echo response processing and analog-to-digital conversion performed based on down-sampling to generate the echo signal ES.

Each of the conversion circuits in the digital-to-analog conversion circuit 120 described above includes a plurality of current sources (not illustrated in the figure) to generate the analog signal according to the control of the corresponding signal feeding. The current sources include thermometer-controlled current sources and binary-controlled current sources each having a current offset such that the analog signal includes a static mismatch error.

The echo calibration circuit 140 cancels the static mismatch error generated from each of the conversion circuits. By using an odd calibration circuit and an even calibration circuit operating at the second frequency and corresponding to the conversion circuits that generate the echo-canceling analog signal included therein, the echo calibration circuit 140 performs mapping according to a plurality of offset tables and perform processing according to a plurality groups of response coefficients on the signal feeding related to an odd input part ISO and an even input part ISE of the input digital signal IS respectively, to generate an odd calibration part and an even calibration part of an echo-canceling calibration signal.

Figure 4:
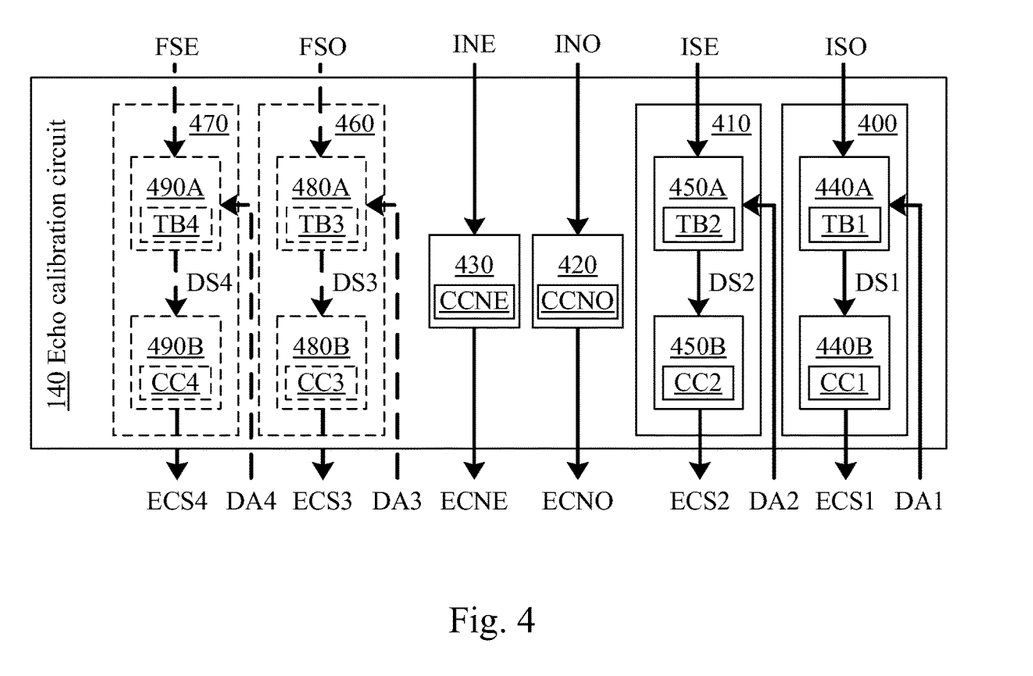
FIG. 4 illustrates a more detailed block diagram of the echo calibration circuit according to an embodiment of the present invention.

Further, the echo calibration circuit 140 further performs processing on the odd pseudo noise digital signal INO and the even pseudo noise digital signal INE according to a group of odd pseudo noise response parameters CCNO and a group of even pseudo noise response parameters CCNE (as illustrated in FIG. 4) to generate an odd pseudo noise calibration signal ECNO and an even pseudo noise calibration signal ECNE.

FIG. 4 illustrates a more detailed block diagram of the echo calibration circuit 140 according to an embodiment of the present invention. The echo calibration circuit 140 includes an odd output echo-canceling calibration circuit 400, an even output echo-canceling calibration circuit 410, an odd pseudo noise calibration circuit 420 and an even pseudo noise calibration circuit 430.

The odd output echo-canceling calibration circuit 400 includes a first mapping circuit 440A and a first response circuit 440B. The first mapping circuit 440A receives and performs mapping on the odd input part ISO of the input digital signal IS according to a first offset table TB1 to generate a first mapped signal DS1. The first response circuit 440B receives and performs processing on the first mapped signal DS1 according to a first group of response coefficients CC1 to generate an odd output echo-canceling calibration signal ECS1.

The even output echo-canceling calibration circuit 410 includes a second mapping circuit 450A and a second response circuit 450B. The second mapping circuit 450A receives and performs mapping on the even input part ISE of the input digital signal IS according to a second offset table TB2 to generate a second mapped signal DS2. The second response circuit 450B receives and performs processing on the second mapped signal DS2 according to a second group of response coefficients CC2 to generate an even output echo-canceling calibration signal ECS2.

In the mapping circuits described above, each of the offset tables includes a plurality of one-to-one corresponding relations between a plurality of codewords and a plurality of codeword offset values. The input codeword corresponds to one of the codewords in the first offset table TB1 and the second offset table TB2. In an initial status, all the codeword offset values are set to be 0.

The odd pseudo noise calibration circuit 420 receives and performs processing on the odd pseudo noise digital signal INO according to a group of odd pseudo noise response coefficients CCNO to generate the odd pseudo noise calibration signal ECNO. The even pseudo noise calibration circuit 430 receives and performs processing on the even pseudo noise digital signal INE according to a group of even pseudo noise response coefficients CCNE to generate the even pseudo noise calibration signal ECNE.

In an embodiment, the digital-to-analog conversion apparatus 100 in FIG. 1 further includes an error calculation circuit 160 to calculate an error signal DIS, which is a difference between the echo signal ES and a sum of the calibration signals described above (i.e., ECS1-ECS2, ECNO and ECNE).

In an embodiment, the digital-to-analog conversion apparatus 100 in FIG. 1 further includes a remained echo-canceling circuit 170 (abbreviated as REC in FIG. 1) to perform echo-canceling on a remained echo. The remained echo-canceling circuit 170 includes a remained echo response circuit 180 (abbreviated as RER in FIG. 1) and a canceling circuit 190.

The remained echo response circuit 180 receives and performs processing on the input digital signal IS according to a group of remained echo response coefficients CCR to generate a remained echo-canceling signal ECR. The canceling circuit 190 performs subtraction on the remained echo-canceling signal ECR and the error signal DIS to generate a final error signal FDIS. The remained echo response circuit 180 makes group of remained echo response coefficients CCR converge according to the final error signal FDIS.

The calibration parameter calculation circuit 150 substantially generates the offsets according to the error signal DIS, which is a difference between the echo signal ES and a sum of the calibration signals described above (i.e., ECS1-ECS2, ECNO and ECNE), and path information related to the echo calibration circuit 140. In an embodiment, the calibration parameter calculation circuit 150 substantially generates the offsets according to the final error signal FDIS after being processed by the remained echo-canceling circuit 170.

In an embodiment, the path information includes the path delays DL1-DL2 of the response circuit (the first response circuit 440B and second response circuit 450B) to the calibration parameter calculation circuit 150. Since the operation of these circuits takes time, the calibration parameter calculation circuit 150 needs to track the calculated offsets to the correct input codeword according to the path delays DL1-DL2.

In an embodiment, the calibration parameter calculation circuit 150 receives the first and the second groups of response coefficients CC1-CC2 of the first and the second response circuits 440B-450B, performs one-dimensional inversion respectively on these response coefficients, multiplies the values of the final error signal FDIS by the inversed response coefficients and accumulates the multiplication results to generate corresponding inverted offsets values. According to the path delays DL1-DL2, the calibration parameter calculation circuit 150 further sets each of the inverted offset values to be the first and the second offsets DA1-DA2 corresponding to the first and the second mapping circuits 440A-450A.

It is appreciated that the generation of the offset values described above is merely an example. In other embodiments, the calibration parameter calculating circuit 150 may generate the offset values by using other methods.

The echo calibration circuit 140 further performs training according to the final error signal FDIS and the pseudo-noise transmission path information from the digital-to-analog conversion circuit 120 to the echo transmission circuit 130 such that each of the groups of response coefficients converges to accomplish the object of performing calibration on the digital-to-analog conversion circuit 120. The pseudo-noise transmission path information can be obtained according to the feeding of the odd pseudo noise digital signal INO and the even pseudo noise digital signal INE and the transmission of the pseudo-noise analog signal ON.

In order to avoid the interaction between the training objects, the digital-to-analog conversion apparatus 100 performs training having different stages.

In a first training stage, the output conversion circuit 300 and the pseudo noise conversion circuit 320 are enabled such that the odd pseudo noise calibration circuit 420 and the even pseudo noise calibration circuit 430 make the odd pseudo noise response coefficients CCNO and the even pseudo noise response coefficients CCNE converge according to the echo signal ES. The first response circuit 440B and second response circuit 450B set the converged odd pseudo noise response coefficients CCNO and the converged even pseudo noise response coefficients CCNE to be the first response coefficients CC1 and the second response coefficients CC2 respectively.

In a second training stage, the output echo-canceling conversion circuit 310 is further enabled to update the first offset table TB1 and the second offset table TB2 according to the first offset DA1 and the second offset DA2 in the offsets related to the odd output echo-canceling calibration circuit 400 and the even output echo-canceling calibration circuit 410.

In an embodiment, the offset values of the current sources included in the output echo-canceling conversion circuit 310 have different combinations generated according to different combinations of the input codewords such that a mapping relation exists between the offset values of the current sources and the offset values of the input codewords. In the second training stage, the calibration parameter calculation circuit 150 distinguishes the offset values that the different input codeword corresponds to into a plurality of value groups according to an operation status of each of the current sources. The calibration parameter calculating circuit 150 further sets each of the current sources to be a target current source to further set a corresponding current offset value calculation formula. The current offset value calculation formula is a subtraction result of two of the value groups such that the current offset value of each of the current sources besides the target current source cancels out in the two value groups.

The calibration parameter calculation circuit 150 substitutes the offset values to the current offset value calculation formula that each of the current sources corresponds to, so as to calculate the current offset value of the target current source. The calibration parameter calculating circuit 150 further converts the current offset value of the current sources to a plurality of codeword offset values to update the corresponding first and the second offset tables TB1-TB2.

In an embodiment, the calibration parameter calculation circuit 150 sets the current offset values of two of current sources to be 0 as anchor points to avoid the interaction of the system.

By using the method described above, the calibration parameter calculating circuit 150 can update the first and the second offset table TB1-TB2 of the first and the second mapping circuit 440A-450A.

In an embodiment, the output echo-canceling conversion circuit 310 may further includes s a control circuit (not illustrated) to sort the current offset values that the current sources correspond to, so as to generate a turn-on order to turn on the current sources according to the input codeword based on the turn-on order by using a thermometer control mechanism such that a linearity of the current sources when the current sources turn on according to the turn-on order is larger than a predetermined value. The setting of the turn-on order can be performed by using different methods and is not described herein.

When the output analog signal OD is transmitted through a transformer, a reflection from the transformer or a mismatch against external impedance may result in echoes to the echo-transmitting path EP that can not be fully canceled by the output echo-canceling analog signal OEC. As a result, in some embodiments, a mismatch echo-canceling circuit can be disposed in the digital-to-analog conversion apparatus 100 to cancel the echoes generated due to the mismatch.

Reference is now made to FIGS. 1-4 at the same time. The circuits related to performing mismatch echo-canceling are illustrated as dashed-line blocks in FIGS. 1-4.

As illustrated in FIG. 2, in some embodiments, the signal input circuit 110 further includes an odd filtering circuit 240 and an even filtering circuit 250 to respectively retrieve and perform filtering on the odd input part ISO and the even input part ISE of the input digital signal IS to output an odd filtered signal FSO and an even filtered signal FSE to the digital-to-analog conversion circuit 120.

Further, the signal input circuit 110 may selectively include a limiting circuit 260 to limit an extremely large value and an extremely small value of the odd filtered signal FSO and the even filtered signal FSE to be a predetermined maximum value and a predetermined minimum value and transmit the maximum value and the minimum value to the digital-to-analog conversion circuit 120.

For example, when a common value of each of the odd filtered signal FSO and the even filtered signal FSE ranges from −6 to +6, a peak error may occur during the subsequent calibration process performed by the calibration circuit when an uncommon value, e.g., −7 or +7 occurs. As a result, the limiting circuit 260 can limit the extremely large values of −7 and +7 to be the predetermined maximum value and the predetermined minimum value of −6 and +6 respectively to avoid the occurrence of peak error.

As illustrated in FIG. 3, the digital-to-analog conversion circuit 120 further includes a mismatch echo-canceling conversion circuit 340 (abbreviated as MECC in FIG. 3) to receive and perform conversion on the odd filtered signal FSO and the even filtered signal FSE to generate a mismatch echo-canceling analog signal MEC.

As illustrated in FIG. 4, the echo calibration circuit 140 further includes an odd mismatch echo-canceling calibration circuit 460 and an even mismatch echo-canceling calibration circuit 470.

The odd mismatch echo-canceling calibration circuit 460 includes a third mapping circuit 480A and a third response circuit 480B. The third mapping circuit 480A receives and performs mapping on the odd filtered signal FSO according to a third offset table TB3 to generate a third mapped signal DS3. The third response circuit 480B receives and performs processing on the third mapped signal DS3 according to a third group of response coefficients CC3 to generate an odd mismatch echo-canceling calibration signal ECS3.

The even mismatch echo-canceling calibration circuit 470 includes a fourth mapping circuit 490A and a fourth response circuit 490B. The fourth mapping circuit 490A receives and performs mapping on the even filtered signal FSE according to a fourth offset table TB4 to generate a fourth mapped signal DS4. The fourth response circuit 490B receives and performs processing on the fourth mapped signal DS4 according to a fourth group of response coefficients CC4 to generate an even mismatch echo-canceling calibration signal ECS4.

Similarly, each of the offset tables includes a plurality of one-to-one corresponding relations between a plurality of codewords and a plurality of codeword offset values. The detail of these offset tables is not described herein.

The error calculation circuit 160 further calculates the error signal DIS, which is a difference between the echo signal ES and a sum of the calibration signal described above, the odd mismatch echo-canceling calibration signal ECS3 and the even mismatch echo-canceling calibration signal ECS4.

Figure 5:
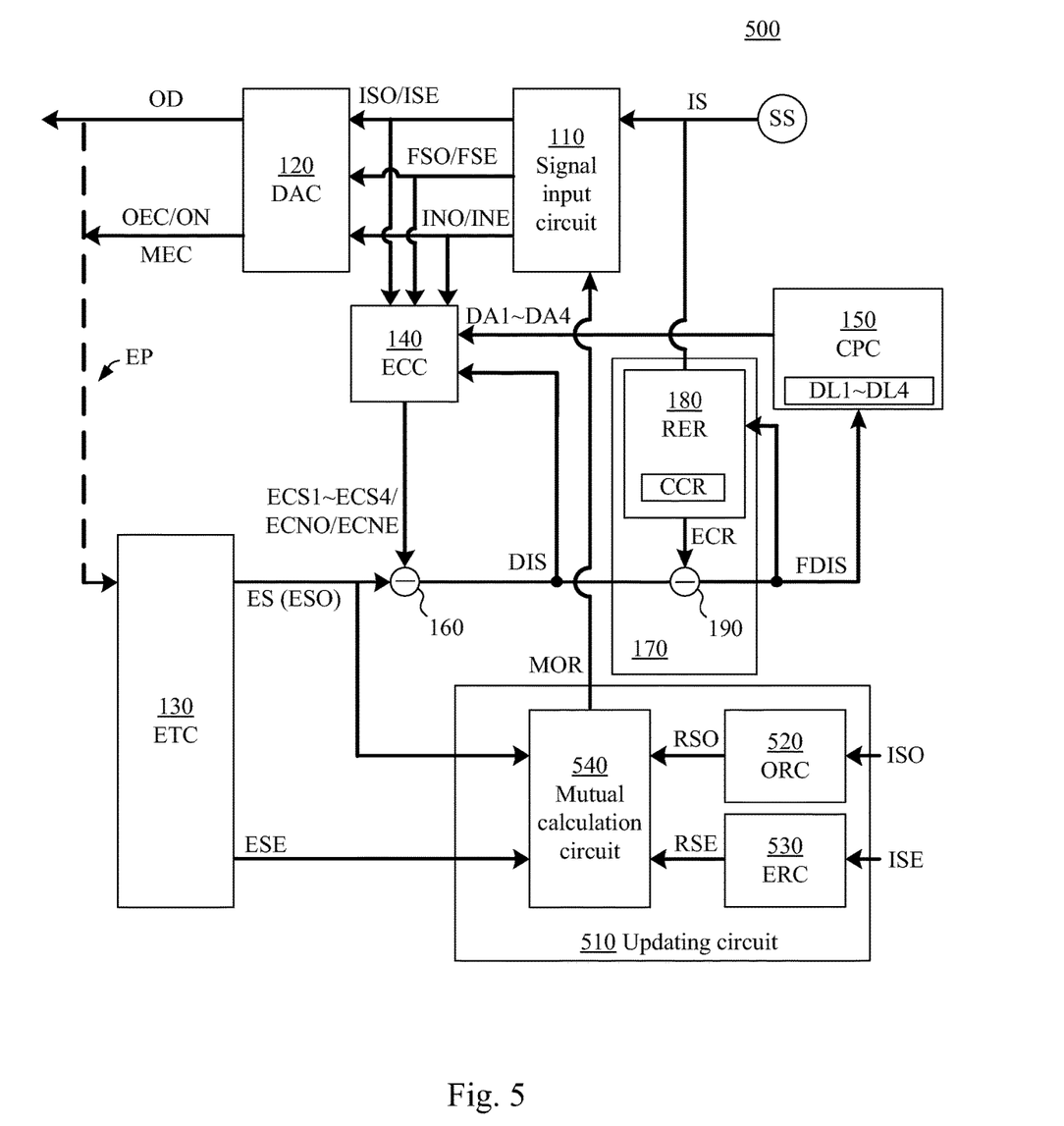
FIG. 5 illustrates a block diagram of a digital-to-analog conversion apparatus according to another embodiment of the present invention.

The calibration parameter calculation circuit 150 generates the offsets according to the final error signal FDIS and path information related to the odd mismatch echo-canceling calibration circuit 460 and the even mismatch echo-canceling calibration circuit 470, i.e., the path delays DL3-DL4 illustrated in FIG. 5 to track the calculated offsets to the correct input codeword according to the path delays DL3-DL4. Further, the calibration parameter calculation circuit 150 receives the third and the fourth groups of coefficients CC3-CC4 of the third and the fourth response circuits 480B-490B, performs one-dimensional inversion respectively on these response coefficients, multiplies the values of the final error signal FDIS by the inversed response coefficients and accumulates the multiplication results to generate corresponding inverted offsets values. According to the path delays DL3-DL4, the calibration parameter calculating circuit 150 further sets each of the inverted offset values to be the third and the fourth offsets DA3-DA4 corresponding to the third and the fourth mapping circuits 480A-490A.

It is appreciated that the generation of the offset values described above is merely an example. In other embodiments, the calibration parameter calculating circuit 150 may generate the offset values by using other methods.

The first training stage performed under the condition that the circuits for performing mismatch echo-canceling are included is similar to the first training stage performed described above. The only difference is that the third response circuit 480B and the fourth response circuit 490B receive and set the converged odd pseudo noise response coefficients CCNO and the converged even pseudo noise response coefficients CCNE to be the third group of response coefficients CC3 and the fourth group of response coefficients CC4 respectively.

The second training stage performed under the condition that the circuits for performing mismatch echo-canceling are included is similar to the second training stage performed described above. The only difference is that the mismatch echo-canceling conversion circuit 340 is also enabled to output the mismatch echo-canceling analog signal MEC and update the third and the fourth offset tables TB3-TB4 according to the related third and the fourth offsets DA3-DA4. In an embodiment, the third and the fourth offset tables TB3-TB4 can selectively be updated according to the feeding of the third and the fourth offsets DA3-DA4 without setting any anchor point. However, the present invention is not limited thereto.

Reference is now made to FIG. 5. FIG. 5 illustrates a block diagram of a digital-to-analog conversion apparatus 500 according to another embodiment of the present invention. The configuration of the digital-to-analog conversion apparatus 500 in FIG. 5 is similar to the configuration of the digital-to-analog conversion apparatus 100 in FIG. 1. The identical components are not described herein.

In the present embodiment, the digital-to-analog conversion apparatus 500 in FIG. 5 includes the circuits for performing mismatch echo-canceling and is equipped with the mechanism that updates the group of odd filtering coefficients FOX of the odd filtering circuit 240 and the group of even filtering coefficients FXE of the even filtering circuit 250 in FIG. 2.

More specifically, two down-sampling circuits (not illustrated in the figure) can be disposed in the echo transmission circuit 130 in FIG. 5 to generate an odd echo signal ESO and an even echo signal ESE having the second frequency. The odd echo signal ESO has an odd sign and the even echo signal ESE has an even sign. In FIG. 5, the odd echo signal ESO is used to perform calculation with the echo-canceling calibration signal to generate the error signal DIS. However, in other embodiments, the even echo signal ESE can also be used to perform calculation with the echo-canceling calibration signal to generate the error signal DIS.

Further, the digital-to-analog conversion apparatus 500 further includes an updating circuit 510. The updating circuit 510 includes an odd response circuit 520 (abbreviated as ORC in FIG. 5), an even response circuit 530 (abbreviated as ERC in FIG. 5) and a mutual calculation circuit 540.

The odd response circuit 520 retrieves and performs response processing on the odd input part ISO of the input digital signal IS to output an odd response signal RSO. The even response circuit 530 retrieves and performs response processing on the even input part ISE of the input digital signal IS to output an even response signal RSE.

The mutual calculation circuit 540 receives the odd response signal RSO, the even response signal RSE, the odd echo signal ESO and the even echo signal ESE. The mutual calculation circuit 540 further performs mutual calculation on the odd response signal RSO, the even response signal RSE, the odd sign of the odd echo signal ESO and the even sign of the even echo signal ESE. Each of the odd sign and even sign may use +1 and −1 to represent a positive sign and a negative sign respectively. The odd sign is respectively used to perform calculation with the odd response signal RSO and the even response signal RSE. The even sign is also respectively used to perform calculation with the odd response signal RSO and the even response signal RSE. Such a mutual calculation generates a mutual calculation result MOR having the first frequency such that the odd filtering circuit 240 and the even filtering circuit 250 update the odd filtering coefficients FOX and the even filtering coefficients FXE according to the mutual calculation result MOR.

As a result, the digital-to-analog conversion apparatus 100 of the present invention generates an output analog signal and an echo-canceling analog signal having a first frequency and perform calibration thereon by using internal circuits that operate in a second frequency, which is a half of the first frequency according to an echo signal through down-sampling.

Figure 6:
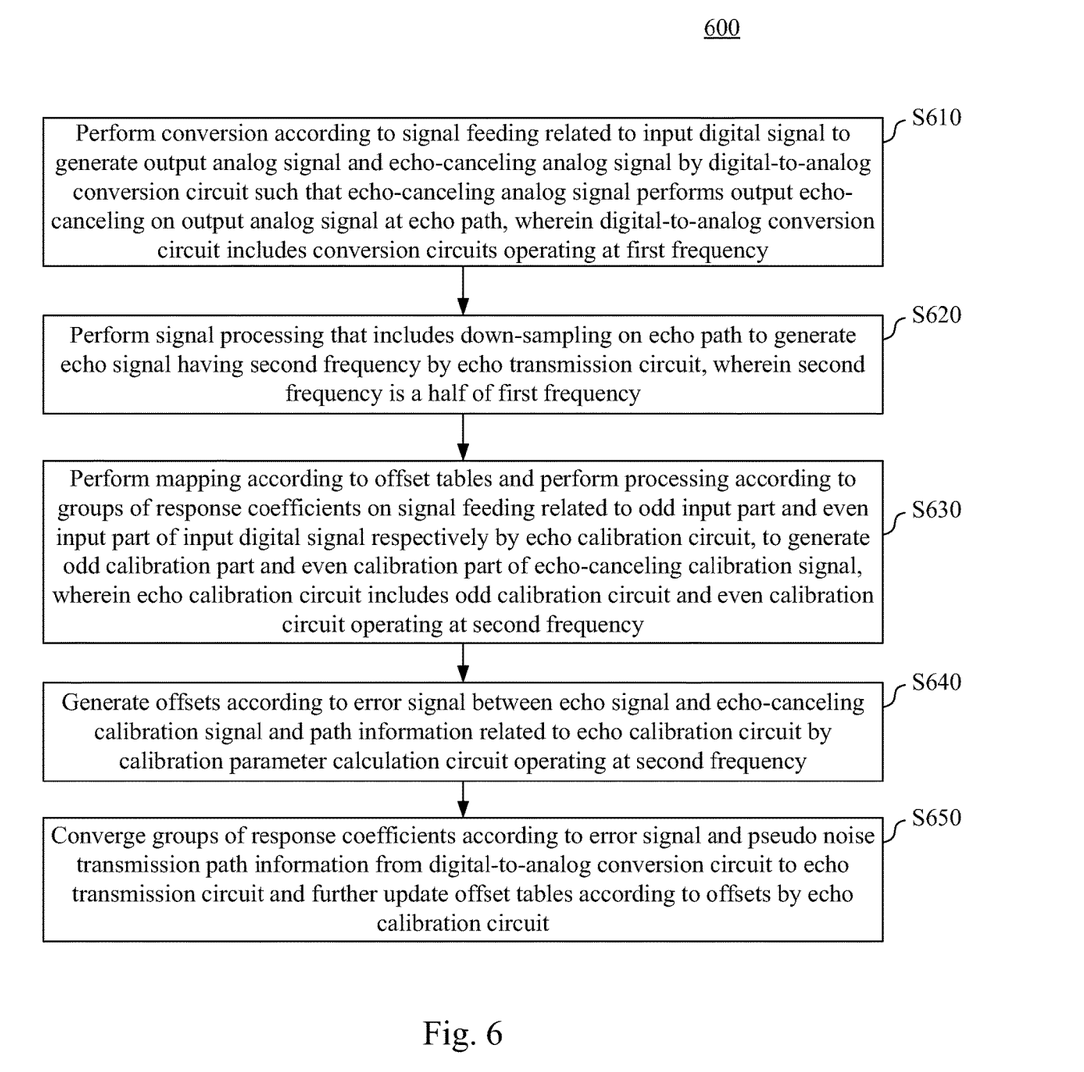
FIG. 6 illustrates a flow chart of a digital-to-analog conversion method having signal calibration mechanism according to an embodiment of the present invention.

Reference is now made to FIG. 6. FIG. 6 illustrates a flow chart of a digital-to-analog conversion method 600 having signal calibration mechanism according to an embodiment of the present invention.

In addition to the apparatus described above, the present disclosure further provides the digital-to-analog conversion method 600 having signal calibration mechanism that can be used in such as, but not limited to, the digital-to-analog conversion apparatus 100 in FIG. 1. As illustrated in FIG. 6, an embodiment of the digital-to-analog conversion method 600 includes the following steps.

In step S610, conversion is performed according to the signal feeding related to the input digital signal IS having the input codeword to generate the output analog signal OD and the echo-canceling analog signal by the digital-to-analog conversion circuit 120 such that the echo-canceling analog signal at least performs output echo-canceling on the output analog signal OD at the echo path EP, wherein the digital-to-analog conversion circuit 120 includes the conversion circuits operating at the first frequency.

In step S620, signal processing that includes down-sampling is performed on the echo path EP to generate the echo signal ES having the second frequency by the echo transmission circuit 130, wherein the second frequency is a half of the first frequency.

In step S630, mapping is performed according to the offset tables and processing is performed according to the groups of response coefficients on the signal feeding related to the odd input part ISO and the even input part ISE of the input digital signal IS respectively by the echo calibration circuit 140, to generate the odd calibration part and the even calibration part of the echo-canceling calibration signal, wherein the echo calibration circuit 140 includes the odd calibration circuit and the even calibration circuit operating at the second frequency and corresponding to the conversion circuits that generate the echo-canceling analog signal.

In step S640, the offsets are generated according to the error signal DIS between the echo signal ES and the echo-canceling calibration signal and path information related to the echo calibration circuit 140 by the calibration parameter calculation circuit 150 operating at the second frequency.

In step S650, the groups of response coefficients are converged according to the error signal ES and the pseudo noise transmission path information from the digital-to-analog conversion circuit 120 to the echo transmission circuit 130 and the offset tables are further updated according to the offsets by the echo calibration circuit 140.

It is appreciated that the embodiments described above are merely an example. In other embodiments, it should be appreciated that many modifications and changes may be made by those of ordinary skill in the art without departing, from the spirit of the disclosure.

In summary, the present invention discloses the digital-to-analog conversion apparatus and the digital-to-analog conversion method having signal calibration mechanism to generate an output analog signal and an echo-canceling analog signal having a first frequency and perform calibration thereon by using internal circuits that operate in a second frequency, which is a half of the first frequency according to an echo signal through down-sampling.

The aforementioned descriptions represent merely the preferred embodiments of the present invention, without any intention to limit the scope of the present invention thereto. Various equivalent changes, alterations, or modifications based on the claims of present invention are all consequently viewed as being embraced by the scope of the present invention.

What is claimed is:

1. A digital-to-analog conversion apparatus having signal calibration mechanism, comprising:
    a digital-to-analog conversion circuit comprising a plurality of conversion circuits operating at a first frequency to perform conversion according to a signal feeding related to an input digital signal having an input codeword to generate an output analog signal and an echo-canceling analog signal, wherein the echo-canceling analog signal at least performs output echo-canceling on the output analog signal at an echo path;
    an echo transmission circuit to perform signal processing that includes down-sampling on the echo path to generate an echo signal having a second frequency, wherein the second frequency is a half of the first frequency;
    an echo calibration circuit comprising an odd calibration circuit and an even calibration circuit operating at the second frequency and corresponding to the conversion circuits that generate the echo-canceling analog signal, wherein the odd calibration circuit and the even calibration circuit perform mapping according to a plurality of offset tables and perform processing according to a plurality groups of response coefficients on the signal feeding related to an odd input part and an even input part of the input digital signal respectively, to generate an odd calibration part and an even calibration part of an echo-canceling calibration signal; and
    a calibration parameter calculation circuit operating at the second frequency to generate a plurality offsets according to an error signal between the echo signal and the echo-canceling calibration signal and path information related to the echo calibration circuit, wherein the echo calibration circuit makes the groups of response coefficients converge according to the error signal and pseudo noise transmission path information from the digital-to-analog conversion circuit to the echo transmission circuit, and further updates the offset tables according to the offsets.

2. The digital-to-analog conversion apparatus of claim 1, further comprising a signal input circuit to perform signal feeding on the digital-to-analog conversion circuit, wherein the signal input circuit comprises:
    an odd feeding circuit to retrieve and output the odd input part of the input digital signal;
    an even feeding circuit to retrieve and output the even input part of the input digital signal;
    an odd pseudo noise generation circuit to generate and feed an odd pseudo noise digital signal to the digital-to-analog conversion circuit; and
    an even pseudo noise generation circuit to generate and feed an even pseudo noise digital signal to the digital-to-analog conversion circuit.

3. The digital-to-analog conversion apparatus of claim 2, wherein the digital-to-analog conversion circuit comprises:
    an output conversion circuit to receive and perform conversion on the odd input part of the input digital signal and the even input part of the input digital signal to generate the output analog signal;
    an output echo-canceling conversion circuit to receive and perform conversion on the odd input part of the input digital signal and the even input part of the input digital signal to generate an output echo-canceling analog signal comprised in the echo-canceling analog signal to the echo path; and
    a pseudo noise conversion circuit to receive and perform conversion on the odd pseudo noise digital signal and the even pseudo noise digital signal to generate a pseudo noise analog signal to the echo path.

4. The digital-to-analog conversion apparatus of claim 3, wherein the echo calibration circuit comprises:
    an odd output echo-canceling calibration circuit comprising:
        a first mapping circuit to receive and perform mapping on the odd input part of the input digital signal according to a first offset table of the offset tables to generate a first mapped signal; and
        a first response circuit to receive and perform processing on the first mapped signal according to a first group of response coefficients of the groups of response coefficients to generate an odd output echo-canceling calibration signal of the echo-canceling calibration signal;
    an even output echo-canceling calibration circuit comprising:
        a second mapping circuit to receive and perform mapping on the even input part of the input digital signal according to a second offset table of the offset tables to generate a second mapped signal; and
        a second response circuit to receive and perform processing on the second mapped signal according to a second group of response coefficients of the groups of response coefficients to generate an even output echo-canceling calibration signal of the echo-canceling calibration signal;
    an odd pseudo noise calibration circuit to receive and perform processing on the odd pseudo noise digital signal according to a group of odd pseudo noise response coefficients to generate an odd pseudo noise calibration signal; and an even pseudo noise calibration circuit to receive and perform processing on the even pseudo noise digital signal according to a group of even pseudo noise response coefficients to generate an even pseudo noise calibration signal.

5. The digital-to-analog conversion apparatus of claim 4, wherein in a first training stage, the output conversion circuit and the pseudo noise conversion circuit are enabled such that the odd pseudo noise calibration circuit and the even pseudo noise calibration circuit make the group of odd pseudo noise response coefficients and the group of even pseudo noise response coefficients converge according to the echo signal, and the first response circuit and the second response circuit set the group of converged odd pseudo noise response coefficients and the group of converged even pseudo noise response coefficients to be the first group of response coefficients and the second group of response coefficients respectively; and in a second training stage, the output echo-canceling conversion circuit is further enabled to update the first offset table and the second offset table according to a first offset and a second offset of the offsets related to the odd output echo-canceling calibration circuit and the even output echo-canceling calibration circuit.

6. The digital-to-analog conversion apparatus of claim 4, wherein the signal input circuit further comprises an odd filtering circuit and an even filtering circuit to respectively retrieve and perform filtering on the odd input part and the even input part of the input digital signal to output an odd filtered signal and an even filtered signal to the digital-to-analog conversion circuit;

the digital-to-analog conversion circuit further comprises a mismatch echo-canceling conversion circuit to receive and perform conversion on the odd filtered signal and the even filtered signal to generate a mismatch echo-canceling analog signal comprised in the echo-canceling analog signal to the echo path; and the echo calibration circuit further comprises:
an odd mismatch echo-canceling calibration circuit comprising:
a third mapping circuit to receive and perform mapping on the odd filtered signal according to a third offset table of the offset tables to generate a third mapped signal; and
a third response circuit to receive and perform processing on the third mapped signal according to a third group of response coefficients of the response coefficients to generate an odd mismatch echo-canceling calibration signal comprised in the echo-canceling calibration signal;
an even mismatch echo-canceling calibration circuit comprising:
a fourth mapping circuit to receive and perform mapping on the even filtered signal according to a fourth offset table of the offset tables to generate a fourth mapped signal; and
a fourth response circuit to receive and perform processing on the fourth mapped signal according to a fourth group of response coefficients of the response coefficients to generate an even mismatch echo-canceling calibration signal comprised in the echo-canceling calibration signal;

wherein in a first training stage, the third response circuit and the fourth response circuit set the group of converged odd pseudo noise response coefficients and the group of converged even pseudo noise response coefficients to be the third group of response coefficients and the fourth group of response coefficients respectively;

in a second training stage, the mismatch echo-canceling conversion circuit is further enabled to update the third offset table and the fourth offset table according to a third offset and a fourth offset of the offsets related to the odd mismatch echo-canceling calibration circuit and the even mismatch echo-canceling calibration circuit.

7. The digital-to-analog conversion apparatus of claim 6, wherein the echo transmission circuit performs down-sampling to generate an odd echo signal and an even echo signal having the second frequency, the odd echo signal having an odd sign and the even echo signal having an even sign, and the digital-to-analog conversion apparatus further comprises an updating circuit comprising:

an odd response circuit to retrieve and perform response processing on the odd input part of the input digital signal to output an odd response signal;
an even response circuit to retrieve and perform response processing on the even input part of the input digital signal to output an even response signal; and
a mutual calculation circuit to update a group of odd filtering coefficients of the odd filtering circuit and a group of even filtering coefficients of the even filtering circuit according to a mutual calculation result among the odd response signal, the even response signal, the odd sign and the even sign.

8. The digital-to-analog conversion apparatus of claim 6, wherein the signal input circuit further comprises a limiting circuit to limit an extremely large value and an extremely small value of the odd filtered signal and the even filtered signal to be a predetermined maximum value and a predetermined minimum value and transmit the maximum value and the minimum value to the digital-to-analog conversion circuit.

9. The digital-to-analog conversion apparatus of claim 1, further comprising a remained echo-canceling circuit comprising:

a remained echo response circuit to receive and perform processing on the input digital signal according to a group of remained echo response coefficients to generate a remained echo-canceling signal; and
a canceling circuit to perform subtraction on the remained echo-canceling signal and the error signal to generate a final error signal;
wherein the remained echo response circuit makes the group of remained echo response coefficients converge according to the final error signal and the calibration parameter calculation circuit substantially generates the offsets according to the final error signal and path information related to the echo calibration circuit.

10. A digital-to-analog conversion method having signal calibration mechanism used in a digital-to-analog conversion apparatus, comprising:

performing conversion according to a signal feeding related to an input digital signal having an input codeword to generate an output analog signal and an echo-canceling analog signal by a digital-to-analog conversion circuit such that the echo-canceling analog signal at least performs output echo-canceling on the output analog signal at an echo path, wherein the digital-to-analog conversion circuit comprises a plurality of conversion circuits operating at a first frequency;

performing signal processing that includes down-sampling on the echo path to generate an echo signal having a second frequency by an echo transmission circuit, wherein the second frequency is a half of the first frequency;

performing mapping according to a plurality of offset tables and performing processing according to a plurality groups of response coefficients on the signal feeding related to an odd input part and an even input part of the input digital signal respectively by an echo calibration circuit, to generate an odd calibration part and an even calibration part of an echo-canceling calibration signal, wherein the echo calibration circuit comprises an odd calibration circuit and an even calibration circuit operating at the second frequency and corresponding to the conversion circuits that generate the echo-canceling analog signal;

generating a plurality offsets according to an error signal between the echo signal and the echo-canceling calibration signal and path information related to the echo calibration circuit by a calibration parameter calculation circuit operating at the second frequency; and making the groups of response coefficients converge according to the error signal and pseudo noise transmission path information from the digital-to-analog conversion circuit to the echo transmission circuit, and further updating the offset tables according to the offsets by the echo calibration circuit.

11. The digital-to-analog conversion method of claim 10, wherein the digital-to-analog conversion apparatus further comprises a signal input circuit to perform signal feeding on the digital-to-analog conversion circuit, the digital-to-analog conversion method further comprising:

retrieving and outputting the odd input part of the input digital signal by an odd feeding circuit of the signal input circuit;

retrieving and outputting the even input part of the input digital signal by an even feeding circuit of the signal input circuit;

generating and feeding an odd pseudo noise digital signal to the digital-to-analog conversion circuit by an odd pseudo noise generation circuit of the signal input circuit; and generating and feeding an even pseudo noise digital signal to the digital-to-analog conversion circuit by an even pseudo noise generation circuit of the signal input circuit.

12. The digital-to-analog conversion method of claim 11, further comprising:

receiving and performing conversion on the odd input part of the input digital signal and the even input part of the input digital signal to generate the output analog signal by an output conversion circuit comprised by the digital-to-analog conversion circuit;

receiving and performing conversion on the odd input part of the input digital signal and the even input part of the input digital signal to generate an output echo-canceling analog signal comprised in the echo-canceling analog signal to the echo path by an output echo-canceling conversion circuit comprised by the digital-to-analog conversion circuit; and receiving and performing conversion on the odd pseudo noise digital signal and the even pseudo noise digital signal to generate a pseudo noise analog signal to the echo pat by a pseudo noise conversion circuit comprised by the digital-to-analog conversion circuit.

13. The digital-to-analog conversion method of claim 12, further comprising:

receiving and performing mapping on the odd input part of the input digital signal according to a first offset table of the offset tables to generate a first mapped signal by a first mapping circuit comprised by an odd output echo-canceling calibration circuit comprised by the echo calibration circuit;

receiving and performing processing on the first mapped signal according to a first group of response coefficients of the groups of response coefficients to generate an odd output echo-canceling calibration signal of the echo-canceling calibration signal by a first response circuit comprised by the odd output echo-canceling calibration circuit comprised by the echo calibration circuit;

receiving and performing mapping on the even input part of the input digital signal according to a second offset table of the offset tables to generate a second mapped signal by a second mapping circuit comprised by an even output echo-canceling calibration circuit comprised by the echo calibration circuit;

receiving and performing processing on the second mapped signal according to a second group of response coefficients of the groups of response coefficients to generate an even output echo-canceling calibration signal of the echo-canceling calibration signal by a second response circuit comprised by the even output echo-canceling calibration circuit comprised by the echo calibration circuit;

receiving and performing processing on the odd pseudo noise digital signal according to a group of odd pseudo noise response coefficients to generate an odd pseudo noise calibration signal by an odd pseudo noise calibration circuit comprised by the echo calibration circuit; and receiving and performing processing on the even pseudo noise digital signal according to a group of even pseudo noise response coefficients to generate an even pseudo noise calibration signal by an even pseudo noise calibration circuit comprised by the echo calibration circuit.

14. The digital-to-analog conversion method of claim 13, further comprising:

in a first training stage, enabling the output conversion circuit and the pseudo noise conversion circuit such that the odd pseudo noise calibration circuit and the even pseudo noise calibration circuit make the group of odd pseudo noise response coefficients and the group of even pseudo noise response coefficients converge according to the echo signal, and the first response circuit and the second response circuit set the group of converged odd pseudo noise response coefficients and the group of converged even pseudo noise response coefficients to be the first group of response coefficients and the second group of response coefficients respectively; and in a second training stage, further enabling the output echo-canceling conversion circuit to update the first offset table and the second offset table according to a first offset and a second offset of the offsets related to the odd output echo-canceling calibration circuit and the even output echo-canceling calibration circuit.

15. The digital-to-analog conversion method of claim 13, further comprising:

respectively retrieving and performing filtering on the odd input part and the even input part of the input digital signal to output an odd filtered signal and an even filtered signal to the digital-to-analog conversion circuit by an odd filtering circuit and an even filtering circuit comprised by the signal input circuit;

receiving and performing conversion on the odd filtered signal and the even filtered signal to generate a mismatch echo-canceling analog signal comprised in the echo-canceling analog signal to the echo path by a mismatch echo-canceling conversion circuit further comprised by the digital-to-analog conversion circuit;

receiving and performing mapping on the odd filtered signal according to a third offset table of the offset tables to generate a third mapped signal by a third mapping circuit comprised by an odd mismatch echo-canceling calibration circuit comprised by the echo calibration circuit;

receiving and performing processing on the third mapped signal according to a third group of response coefficients of the response coefficients to generate an odd mismatch echo-canceling calibration signal comprised in the echo-canceling calibration signal by a third response circuit comprised by the odd mismatch echo-canceling calibration circuit comprised by the echo calibration circuit;

receiving and performing mapping on the even filtered signal according to a fourth offset table of the offset tables to generate a fourth mapped signal by a fourth mapping circuit comprised by an even mismatch echo-canceling calibration circuit comprised by the echo calibration circuit;

receiving and performing processing on the fourth mapped signal according to a fourth group of response coefficients of the response coefficients to generate an even mismatch echo-canceling calibration signal comprised in the echo-canceling calibration signal by a fourth response circuit comprised by the even mismatch echo-canceling calibration circuit comprised by the echo calibration circuit;

in a first training stage, setting the group of converged odd pseudo noise response coefficients and the group of converged even pseudo noise response coefficients to be the third group of response coefficients and the fourth group of response coefficients respectively by the third response circuit and the fourth response circuit; and in a second training stage, further enabling the mismatch echo-canceling conversion circuit to update the third offset table and the fourth offset table according to a third offset and a fourth offset of the offsets related to the odd mismatch echo-canceling calibration circuit and the even mismatch echo-canceling calibration circuit.

16. The digital-to-analog conversion method of claim 15, further comprising:
performing down-sampling by the echo transmission circuit to generate an odd echo signal and an even echo signal having the second frequency, the odd echo signal having an odd sign and the even echo signal having an even sign;

retrieving and performing response processing on the odd input part of the input digital signal to output an odd response signal by an odd response circuit comprised by an updating circuit comprised by the digital-to-analog conversion apparatus;

retrieving and performing response processing on the even input part of the input digital signal to output an even response signal by an even response circuit comprised by the updating circuit; and updating a group of odd filtering coefficients of the odd filtering circuit and a group of even filtering coefficients of the even filtering circuit according to a mutual calculation result among the odd response signal, the even response signal, the odd sign and the even sign by a mutual calculation circuit comprised by the updating circuit.

17. The digital-to-analog conversion method of claim 15, further comprising:
limiting an extremely large value and an extremely small value of the odd filtered signal and the even filtered signal to be a predetermined maximum value and a predetermined minimum value and transmit the maximum value and the minimum value to the digital-to-analog conversion circuit by a limiting circuit comprised by the signal input circuit.

18. The digital-to-analog conversion method of claim 10, further comprising:
receiving and performing processing on the input digital signal according to a group of remained echo response coefficients to generate a remained echo-canceling signal by a remained echo response circuit comprised by a remained echo-canceling circuit;

performing subtraction on the remained echo-canceling signal and the error signal to generate a final error signal by a canceling circuit comprised by the remained echo-canceling circuit; and making the group of remained echo response coefficients converge according to the final error signal by the remained echo response circuit and substantially generating the offsets according to the final error signal and path information related to the echo calibration circuit by the calibration parameter calculation circuit.

* * * * *